United States Patent [19]

Jacobus et al.

[11] 4,442,421
[45] Apr. 10, 1984

[54] SEMICONDUCTING COORDINATION POLYMERS AND ELECTRICAL APPLICATIONS THEREOF

[76] Inventors: Otha J. Jacobus, 917 Marlene Dr., Gretna, La. 70053; Donald R. Owen, 8418 Sycamore St., New Orleans, La. 70118

[21] Appl. No.: 288,884

[22] Filed: Jul. 31, 1981

[51] Int. Cl.$^3$ .............................................. H01L 7/00
[52] U.S. Cl. .................................... 338/35; 252/518; 528/395; 528/422
[58] Field of Search ......................... 338/35; 252/518; 340/602; 528/395, 422

[56] References Cited

U.S. PATENT DOCUMENTS

| | | | |
|---|---|---|---|
| 3,891,958 | 6/1975 | Wakabayashi | 338/35 |
| 4,145,523 | 3/1979 | Siegl | 528/395 |
| 4,230,604 | 10/1980 | Wingrave | 252/518 |
| 4,312,965 | 1/1982 | Jachimowicz et al. | 528/422 X |

*Primary Examiner*—C. L. Albritton
*Attorney, Agent, or Firm*—C. Emmett Pugh

[57] ABSTRACT

A unique semiconductive, polymeric material capable of use for example as a humidity sensing detector or as an electrical "rectifying-type" element created by pressure treating an oxidized coordination polymer formed from a polydentate organic ligand, such as for example 1,2,4,5-tetraaminobenzene, and a metal salt, such as for example nickle(II) chloride, palladium(II) chloride, or platinum(II) chloride. The element is mounted on a non-conducting base, electrical leads are attached to the element, and the wired element is placed in an electrical circuit capable of for example detecting electrical resistance. The presence of water vapor in the atmosphere about the element elicits rapid, reversible, reproducible changes in the resistance of the element. The wired element can also be used as a "rectifyer-type" element in that it has an electrical polarization which is not instantaneously reversible with a change in voltage polarity.

5 Claims, 1 Drawing Figure

SEMICONDUCTING COORDINATION POLYMERS AND ELECTRICAL APPLICATIONS THEREOF

BACKGROUND OF THE INVENTION

1. Field of the Invention

The invention relates to a unique composition of matter of a semiconductive polymeric material, and to humidity sensors and a method of making a humidity sensor from semiconductive coordination polymers, and to "rectifyer-type" electrical elements and to a method of making an electrical "rectifying-type" element from semiconductive coordination polymers.

2. Prior Art

A. Humidity Sensing

Devices capable of the measurement of humidity have numerous industrial, medical, military and agricultural applications. Commonly employed devices include wet and dry bulb thermometers, hair hydrometers, and certain solid state devices.

Among the solid state devices are those described in U.S. Pat. No. 2,613,302 (issued Oct. 7, 1952, to A. M. Gurewitsch, assignor to General Electric Company), comprising a conducting solid film (perhaps a tin oxide) deposited on a non-conducting base; U.S. Pat. No. 2,740,032 (issued Mar. 27, 1956, to G. J. Bouyoucos), comprising a conducting solid embedded in a non-conducting matrix (e.g. resin impregnated plaster); U.S. Pat. No. 3,295,088 (issued Dec. 27, 1966, to W. J. Smith), comprising a conducting solid embedded in a non-conducting matrix (e.g. copolymer of vinylene carbonate and vinyl acetate); U.S. Pat. No. 3,299,387 (issued Jan. 17, 1967, to R. A. Sanford), comprising a non-conducting solid doped with a semiconductor; U.S. Pat. No. 3,848,218 (issued Nov. 12, 1974 to T. Wakabayashi et al), comprising a humidity sensitive film having finely divided conductive particles dispersed in a resin consisting of a reaction product of a chlorine containing polymer and a polyamide resin (note also related U.S. Pat. No. 3,891,958 issued to T. Wakabayashi assigned to Matsushita Electric Industrial Co., Ltd.); U.S. Pat. No. 4,025,892 (issued May 24, 1977 to J. Pompei et al assigned to U.S. Philips Corp.), comprising a layer of semiconductor material (e.g. zinc oxide); and U.S. Pat. No. 4,052,691 (issued Oct. 4, 1977) to K. Nagand et al assigned to Asahi Glass Co., Ltd.), comprising an orthophosphate coating.

Similarly, solid state devices have been produced which sense specific chemical species other than water. For example, U.S. Pat. No. 3,625,756 (issued Dec. 7, 1971, to N. Taguchi) described a method for making gas sensing elements with a semiconductive material (e.g. $SnO_2$, $NiO$ or $Cr_2O_3$); U.S. Pat. No. 3,879,985 (issued Apr. 29, 1975, to C. G. Maslen) describes a specific device using an n-type semiconductor metal oxide (namely zinc oxide doped with 2% platinum) for the detection of hexane and other organic vapors; and U.S. Pat. No. 4,236,307 (issued Dec. 2, 1980, to Colla, et al, assignor to Johnson Controls Inc.) describes a specific device utilizing a semiconductive polymer film (e.g. a pyrolyzed polyaromatic polymer) for the detection of nitrogen dioxide.

The humidity detectors described above consist, generally, of a conducting solid deposited, embedded, or doped onto a non-conducting base or matrix. They are, by their method of preparation, heterogeneous mixtures or dispersions of conductors in or on non-conductors. Further, the response of these devices to broad ranges of humidity is limited and most are adversely affected by atmospheric pollutants.

SUMMARY DISCUSSION OF THE INVENTION

The present invention is directed to the making of a unique composition of matter of a semiconductive, polymeric material capable of for example detecting humidity under a variety of conditions. In accordance with the invention an oxidized coordination polymer is produced which is pressure treated to provide elements ("chips") which are semiconducting. With appropriate electronic circuitry, the semiconducting element exhibits large resistance responses to small changes in humidity. Additionally, the material temporarily exhibits "rectifer-type" characteristics in that it has an electrical polarization which is not instantaneously reversible with a change in the applied voltage polarity.

BRIEF DESCRIPTION OF THE DRAWINGS

For a further understanding of the nature and objects of the present invention, reference should be had to the following detailed description, taken in conjunction with the accompanying drawing, wherein.

DESCRIPTION OF PREFERRED EMBODIMENTS

Figure 1:
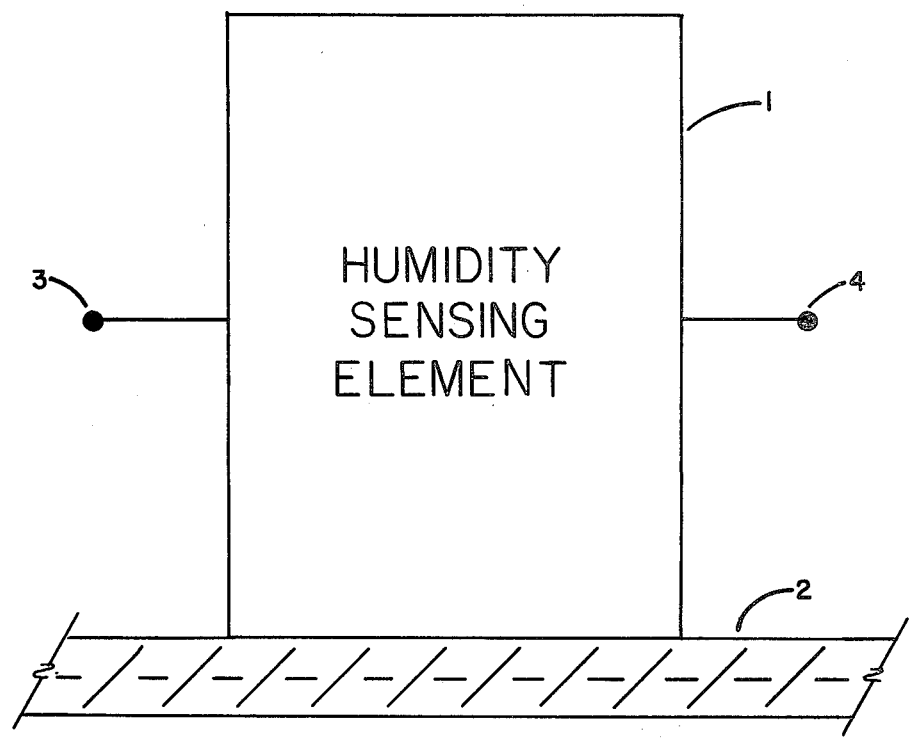
FIG. 1 is a side, generalized view of the preferred embodiment of the present invention.

Numerous coordination complexes of various metal ions are known; these generally consist of a central metal atom or ion surrounded by a coordination sphere of neutral atoms, neutral molecules, or ions. The atoms, molecules, or ions surrounding the central metal are referred to as ligands. The coordination number, that is the number of nearest neighboring groups to the central metal, may vary from metal to metal. Generally these coordination complexes are monomeric.

Selection of groups possessing properly disposed ligands may lead to coordination polymers. For example, if ethylenediamine is added in a 2:1 molar ratio to copper(II) chloride, the monomeric coordination complex

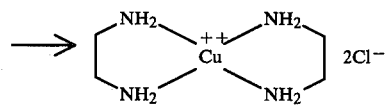

is formed. However, if 1,2,4,5-tetraaminobenzene is added in a 1:1 molar ratio to copper(II) chloride, the polymeric coordination complex

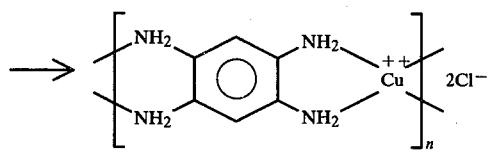

is formed. It is this latter class of materials, that is coordination polymers, which are described herein. These compositions of matter are unique in that they are homogeneous compounds; the disposition of the metal within the organic matrix is controlled by the disposition of the ligands.

EXAMPLE A (Ni)

A solution containing 0.0176 moles of 1,2,4,5-tetraaminobenzene in 50 ml of water is prepared by neutralization of 5.00 g of 1,2,4,5-tetraaminobenzene tetrahydrochloride with 2.82 g of sodium hydroxide in 50 ml of water. To the cooled, stirred, nitrogen flushed solution of tetraaminobenzene is added a solution of 4.18 g. of $NiCl_2.6H_2O$ in 25 ml of water. There is immediately precipitated a light purple solid. The purple solid is isolated by vacuum filtration and it is washed with ethyl alcohol and ether until it is a free flowing purple powder.

EXAMPLE B (Cu)

The procedure of Example A is repeated with the exception that 3.00 g of $CuCl_2.2H_2O$ is substituted for $NiCl_2$. The product in this example is a dark red-brown solid.

EXAMPLE C (Ni+10K Pressure)

The purple coordination polymer described in Example A is placed in a pellet press at 10,000 ppsi pressure yielding purple pellets from which chips are cut of dimensions $1/16 \times 1/16 \times 1/32$ inch. The chip is affixed to a non-conducting base (glass) and electric leads are affixed to opposite sides of the chip with conducting silver paint. The resistance of the chip in this instance is greater than $10^{14}$ ohm, thus effectively functioning as an insulator, and is not affected by humidity.

EXAMPLE D (Cu+10K Pressure)

The red-brown coordination polymer described in Example B is treated according to the procedure described in Example C. The resistance of the chip in this instance in greater than $10^{14}$ ohm and is not affected by humidity.

EXAMPLE E (Ni+Oxidation+10K Pressure)

The purple coordination polymer described in Example A is subjected to an oxidation process in aqueous suspension or in the solid state. In an exemplary oxidation process an aqueous suspension was heated to boiling and molecular oxygen was bubbled through the suspension until a color change from purple to black was complete. Alternatively, over much longer periods of time, heating of the suspension in air achieves the same oxidating process. Similar oxidation can be noted at room temperature in aqueous suspension by utilization of hydrogen peroxide. During this process the polymer changes in color from purple to black. This latter modified polymer is isolated and dried. The dried polymer is black in color.

The black polymer is placed in a pellet press at 10,000 ppsi pressure yielding black pellets.

It is noted that the non-conducting pellets disclosed in Example C slowly oxidize in air, changing from purple to black, resulting in pellets similar to those just described.

A chip 1 (note FIG. 1) is cut out of the black pellets of dimensions $\frac{1}{8} \times \frac{1}{8} \times 1/32$ inch. The chip is affixed to a non-conducting base 2 (for example glass) with any of a number of epoxy resins and electric leads 3, 4 are affixed to opposite sides of the square chip with conducting silver paint. The resistance of the chip in this instance varies generally linearly with the humidity in the mid-part of the humidity scale (note table below). For the described chip the resistance at 100% relative humidity is ca. $5 \times 10^6$ ohms, while at 0% relative humidity it is ca. $5 \times 10^9$ ohms. Further, the chip shows rapid, reversible, reproducible resistance changes as a function of humidity.

| Relative Humidity (%) | Resistance (Megohms) |
|---|---|
| 100.0 | 5 |
| 73 | 8 |
| 51 | 14 |
| 48 | 18 |
| 46 | 30 |
| 45 | 40 |
| 42 | 100 |
| 40 | 200 |
| 37 | 400 |
| 29 | 1,000 |
| 16 | 2,000 |
| 0 | 5,000 |

Resistance measurements were conducted with a "Non-linear Electronics" Model 20 Multimeter in the "megohms" and "nanosiemens" ranges.

The nature of the non-conducting base, method of affixing the chip to the base or the method of affixing the electric leads to the chip do not markedly affect the resistance response of the semiconducting polymer to humidity.

EXAMPLE F (Cu+Oxidation+10K Pressure)

Treatment of the red-brown polymer described in Example B to the procedure described in Example E yields chips which are non-conducting and are unaffected by humidity changes.

EXAMPLE G (Ni+Oxidation+1K Pressure)

The pre-pressurized, oxidized, black nickel-tetraaminobenzene polymer described in the first paragraph of Example E was subjected to 1,000 psi pressure in a pellet press to produce solid wafers from which chips of dimensions ca. $\frac{1}{8} \times \frac{1}{8} \times 1/16$ inch were fashioned. Attachment of electrical leads produced a humidity sensitive element similar to that described in Example E.

EXAMPLE H (Pd+Oxidation+10K Pressure)

A solution of 3.21 g of 1,2,4,5-tetraaminobenzene tetrahydrochloride in 50 ml of distilled water was treated with a solution of 1.81 g of sodium hydroxide in 5 ml of water. A slurry of 2.0 g of palladium (II) chloride in 5 ml of water was added to the tetraaminobenzene solution. The resultant mixture was stirred for 24 hours while air was bubbled through the solution. During this period a black precipitate formed. The precipitate was collected by vacuum filtration and was washed with absolute ethanol and ether. The black product was air dried.

A sample of this palladium-tetraaminobenzene polymer was subjected to 10,000 psi pressure to form a solid wafer. Connection of electrical leads with conducting cement to a chip of the material ca. ⅛×⅛×1/16 inch produced a chip that exhibited humidity sensitivity similar to that described in Example E.

EXAMPLE I (Pt+Oxidation+10K Pressure)

A solution of 2.13 g of 1,2,4,5-tetraaminobenzene tetrahydrochloride in 50 ml of distilled water was treated with a solution of 1.2 g of sodium hydroxide in 5 ml of water. To this solution was added 2.0 g of platinum (II) chloride. The resultant mixture was stirred for 24 hours at room temperature while air bubbled through the reaction mixture. The black precipitate which formed during this period was isolated, washed with absolute ethanol and ether, and air dried.

A sample of this platinum-tetraaminobenzene polymer was subjected to 10,000 psi pressure to form a solid wafer. Connection of electrical leads with conducting cement to a chip of the material ca. ⅛×⅛×1/32 inch produced a humidity sensitive element with properties similar to that described in Example E.

EXAMPLE J (Electrical Polarization)

The electrical polarization of the sensing element chip described in Example E was determined as follows: while cycling a chip from low to high humidity, during which process the resistance of the chip is decreasing, the electrical leads of the test meter are reversed. The resistance at first increases, then stops, and finally reverses to attain the normal equilibrium position. Similar, reverse behavior is noted when the leads are reversed in a high to low humidity run. Recovery times for reversal of polarization are ca. one minute for the chip described in Example E.

Thus, the coordination polymer formed from 1,2,4,5-tetraaminobenzene and nickel(II) chloride, as well as palladium (II), platinum (II), each exhibits resistance responses to changes in humidity with an oxidative treatment (applied or allowed) and processing into pressurized pellets. Chemical analogy would dictate that other polydentate ligands in combination with these metal salts (Ni, Pd, Pt) would exhibit similar response. Among the analogous polydentate ligands would be polyamino polyhydroxy organic compounds, polyhydroxy organic compounds, poly-amino-polycarboxy organic compounds, and polyhydroxy-polycarboxy organic compounds, producing coordination polymers of the general formula

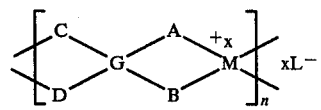

where A, B, C, and D are selected from the groups amino ($NH_2$), hydroxy (OH), or carboxy ($CO_2^-$), G is the central atom or group of atoms to which the groups A, B, C, and D are bonded, M is a metal ion or atom, and L is a ligand required to meet the valence demands of M. The groups A, B, D, and D may all be identical or may consist of various combinations of amino, hydroxy, and carboxy groups. These coordination polymers are unique relative to previously described solid state devices in terms of their defined composition and homogenerity.

The tetraaminobenzene —Ni(II) chloride, —Pd(II), —Pt(II) coordination polymers upon oxidation and pressure processing yield black, gold-colored surfaced solid state elements which when supplied with electric leads exhibit large changes in resistance with small changes in the humidity in the atmosphere about the element.

The oxidation can be achieved either before or after pressurizing and can be applied during the chemical production of the polymeric material or after the pressurizing of the material by for example exposing it to air over a period of time or otherwise treating it with an oxidizing agent.

With respect to pressure, a sufficient amount should be applied to compact the polymeric material to form a continuous or contiguous surface, changing the powdered, dried polymeric percipitate to a non-granulated substance.

Because many varying and different embodiments may be made within the scope of the inventive concept herein taught, and because many modifications may be made in the embodiment herein detailed in accordance with the descriptive requirements of the law, it is to be understood that the details herein are to be interpreted as illustrative and not in a limiting sense.

What is claimed is:

1. A humidity sensing detector, comprising:
    a semiconducting, oxidized coordination polymer, humidity sensing element prepared from a polydentate organic ligand and a metal salt; and
    electrical contacts at spaced locations on said sensing element.
2. The detector of claim 1, wherein there is further included a non-conducting base to which said humidity sensing element is attached.
3. The detector of claim 1, wherein the polydentate organic ligand is selected from the group consisting of polyamino organic compounds, polyamino polyhydroxy organic compounds, polyhydroxy organic compounds, polyamino polycarboxy organic compounds, and polyhydroxy polycarboxy organic compounds, and the metal salt has a metal ion selected from the group consisting of nickel(II), palladium(II), and platinum(II).
4. The detector of claim 3, wherein said polydentate organic ligand is 1,2,4,5-tetraaminobenzene.
5. The detector of either one of claims 3 or 4, wherein said metal salt is nickel(II) chloride.

* * * * *